United States Patent

Shelledy

[11] Patent Number: 5,806,278
[45] Date of Patent: Sep. 15, 1998

[54] DISPENSER FOR SEALED WRAPPED ARTICLES

[76] Inventor: Guy R. Shelledy, 618 Ash St., Summersville, W. Va. 26651

[21] Appl. No.: 784,111

[22] Filed: Jan. 15, 1997

Related U.S. Application Data

[60] Provisional application No. 60/009,967, Jan. 16, 1996.
[51] Int. Cl.⁶ ..................................... B65B 43/26
[52] U.S. Cl. .......................... 53/381.1; 53/381.2; 53/390; 53/384.1; 414/412
[58] Field of Search .......................... 221/31, 26; 53/412, 53/390, 384.1, 381.2, 381.1; 414/412

[56] References Cited

U.S. PATENT DOCUMENTS

| | | | |
|---|---|---|---|
| D. 347,137 | 5/1994 | McWhirter | D6/567 |
| 3,674,176 | 7/1972 | Sagi | 221/26 |
| 3,972,157 | 8/1976 | Meyers | 53/384.1 |
| 4,217,743 | 8/1980 | Escales et al. | 53/381.6 |
| 4,946,339 | 8/1990 | Berg et al. | 53/381.2 |
| 5,118,007 | 6/1992 | Lewis et al. | 221/30 |
| 5,119,969 | 6/1992 | Haber | 414/412 |
| 5,249,705 | 10/1993 | Gates | 221/26 |
| 5,336,034 | 8/1994 | Hidding | 414/412 |
| 5,358,140 | 10/1994 | Pellegrino | 221/26 |
| 5,400,699 | 3/1995 | Cailbault | 221/31 |
| 5,435,459 | 7/1995 | Huck et al. | 221/70 |
| 5,447,253 | 9/1995 | Williams | 221/92 |

FOREIGN PATENT DOCUMENTS

| | | | |
|---|---|---|---|
| 0283448 | 9/1988 | European Pat. Off. | 221/26 |

*Primary Examiner*—James F. Coan
*Assistant Examiner*—Gene L. Kim
*Attorney, Agent, or Firm*—Webb Ziesenheim Bruening Logsdon Orkin & Hanson, P.C.

[57] ABSTRACT

A dispenser for wrapped packages each containing an article and having an edge. The dispenser includes a housing defining a package receiving chamber, the housing including (i) a wall with an outer surface and an inner surface, (ii) a first end longitudinally spaced from a second end and (iii) a first opening defined at the second end for removal of the packages. A biasing member is secured to the housing and positioned within the package receiving chamber. The biasing member is adapted to urge the packages in a first longitudinal direction toward the second end. An aligning member is secured to the housing and positioned adjacent the first opening, and a cutting member having a cutting edge is secured to the housing. The biasing member urges the packages toward the first opening so that a package can be pulled through the first opening while the aligning member positions the article contained within the wrapped package away from the cutting member so that the wrapped package can be cut open by the cutting member edge without the cutting edge contacting the article for removal of the article from the cut-open wrapped package.

17 Claims, 2 Drawing Sheets

DISPENSER FOR SEALED WRAPPED ARTICLES

CROSS REFERENCE TO RELATED APPLICATION

This application claims the benefit of earlier filed United States Provisional Patent Application Ser. No. 60/009,967, filed on Jan. 16, 1996.

BACKGROUND OF THE INVENTION

1. Field of the Invention

The present invention relates to dispensers for sealed wrapped articles.

2. Description of the Prior Art

Individually wrapped articles such as condoms, sutures, bandages and the like are typically packaged in boxes. The user of the article must open the box and withdraw an individual package. Each individual package must then be opened to release its contents. Access to the wrapped contents thus often is inconvenient and cumbersome.

The use of condoms is now commonly promoted to avert the spread of the AIDS virus and other sexually transmitted diseases. However, as condoms are currently packaged and dispensed, they are often inconvenient and difficult to use. Condoms are typically stored in purses, wallets, bathroom cabinets, under the bed and in many other inconvenient places which discourage their use when actually needed. It can be difficult for the user to locate and unwrap a condom from its cumbersome packaging especially in a poorly lit (nighttime) environment. These difficulties reduce the likelihood of the use of condoms. Substantial social benefits would result if a dispenser was available to unwrap and dispense a condom making it easier to use and thus increase its frequency of use.

In the medical environment such as in a doctor's office or emergency room, condoms for use with ultrasound equipment as well as sutures and bandages and the like are normally wrapped in individual packages contained within a box. Medical personnel must search for a box, find an individual item and open the wrapped package to release its contents. This procedure likewise is cumbersome and inconvenient for medical personnel, particularly when latex gloves are worn.

Currently available dispensers of wrapped articles typically suffer from the disadvantages that once dispensed, the wrapped articles must still be unwrapped by the user, adding frustration or error if time is of the essence to the user. This problem is compounded if multiple dispensing is necessary in a short period of time.

In an attempt to overcome these problems, the condom dispenser disclosed in. U.S. Pat. No. 5,435,459 provides for the release of individual wrapped condoms from a housing. Each of the condoms loaded into the housing includes a pull tab on one end and an elongated tab on the other end attached to the base of the housing. When the pull tab is drawn out through an opening in the housing, the condom is dispensed through the opening. A major drawback to this dispenser is that it requires specialized condoms, namely, those with pull tabs on one end and a modification on the other end so that the condoms can be attached to the housing.

Unmodified condoms may be dispensed from the device disclosed in U.S. Pat. No. 5,447,253. The condom dispenser has a slanting floor. The condoms are loaded through the top of the dispenser and gravity fed through a dispensing front opening at the bottom of the dispenser.

Neither of the devices disclosed in U.S. Pat. Nos. 5,435,459 or 5,447,253 alleviate the problem of opening a wrapped package while it is being dispensed. Although U.S. Pat. No. 5,118,007 discloses a dispenser for tablets provided in a roll in which the roll is opened within the dispenser and tablets are released from the top of the dispenser, there is no teaching on how to open a series of wrapped packages dispensed from a container.

None of the dispensers of the prior art describe the release of an individual article from its individual wrapper by opening or cutting the enclosure as the user removes the wrapped article from the dispenser. Accordingly, it is an object of the present invention to provide a dispenser for individually wrapped articles which enhances the ease with which a sealed article is delivered to the user and which facilitates and/or encourages the use of the article.

SUMMARY OF THE INVENTION

The present invention includes a dispenser for wrapped packages each containing an article. The dispenser includes a housing defining a package receiving chamber, the housing including (i) a wall with an outer surface and an inner surface, (ii) a first end longitudinally spaced from a second end and (iii) a first opening defined at the second end for removal of the packages. A biasing member, such as a spring, is secured to the housing and positioned within the package receiving chamber. The biasing member is adapted to urge the packages in a first longitudinal direction toward the second end.

An aligning member is secured to the housing and positioned adjacent the first opening, and a cutting member having a cutting edge is secured to the housing. The cutting member preferably includes a pair of axially spaced cutting disks. The biasing member is adapted to urge the packages toward the first opening so that a package can be pulled through the first opening, the aligning member positioning the article contained within the wrapped package away from the cutting member so that the wrapped package can be cut open by the cutting member edge without the cutting edge contacting the article for removal of the article from the cut-open wrapped package.

The aligning member includes a pair of longitudinally spaced aligning wheels having aligning member surfaces with at least a portion of one of the aligning member surfaces converging towards the other of the aligning member surfaces in a second longitudinal direction. The aligning wheels are rotatably mounted to the housing. In the preferred embodiment, the cutting member is disposed adjacent the aligning member.

The dispenser further includes a first guiding member secured to the housing and positioned adjacent the first opening. The first guiding member is adapted to position the edge of the package adjacent the cutting member edge. The first guiding member includes a pair of longitudinally spaced guiding wheels having guiding member surfaces with at least a portion of one of the guiding member surfaces converging towards the other of the guiding member surfaces in the second longitudinal direction. The guiding wheels are rotatably mounted to the housing.

The dispenser further includes a roller extending along a longitudinal axis rotatably mounted to the housing and adjacent the aligning member such that the roller is adapted to rotate about the longitudinal axis when the package is pulled through the first opening and contacts the roller.

The dispenser preferably also includes a second pair of longitudinally spaced guiding wheels having guiding member surfaces with at least a portion of each of the second longitudinally spaced guiding member surfaces converging towards the other of the second pair of longitudinally spaced guiding member surfaces in the second longitudinal direction. The second pair of guiding wheels are rotatably mounted to the housing. The first and second guiding members are secured to the housing and positioned near the opposite ends of the roller.

A chute is mounted on the outer surface of the wall adjacent the roller and is adapted to receive the packages. A lid is secured to the housing and defines with the housing the first opening. The lid includes a U-shaped inner rim having an edge adjacent the wall and defining a second opening. The first opening is defined as a front opening positioned between the edge of the U-shaped rim and the wall.

The dispenser further includes a tab extending from the wall inner surface into the chamber and adapted to retain one of the packages at a distance from the lid. The dispenser also includes a cover pivotally secured to the lid and a light source mounted to the cover.

DESCRIPTION OF THE PREFERRED EMBODIMENT

Figure 1:
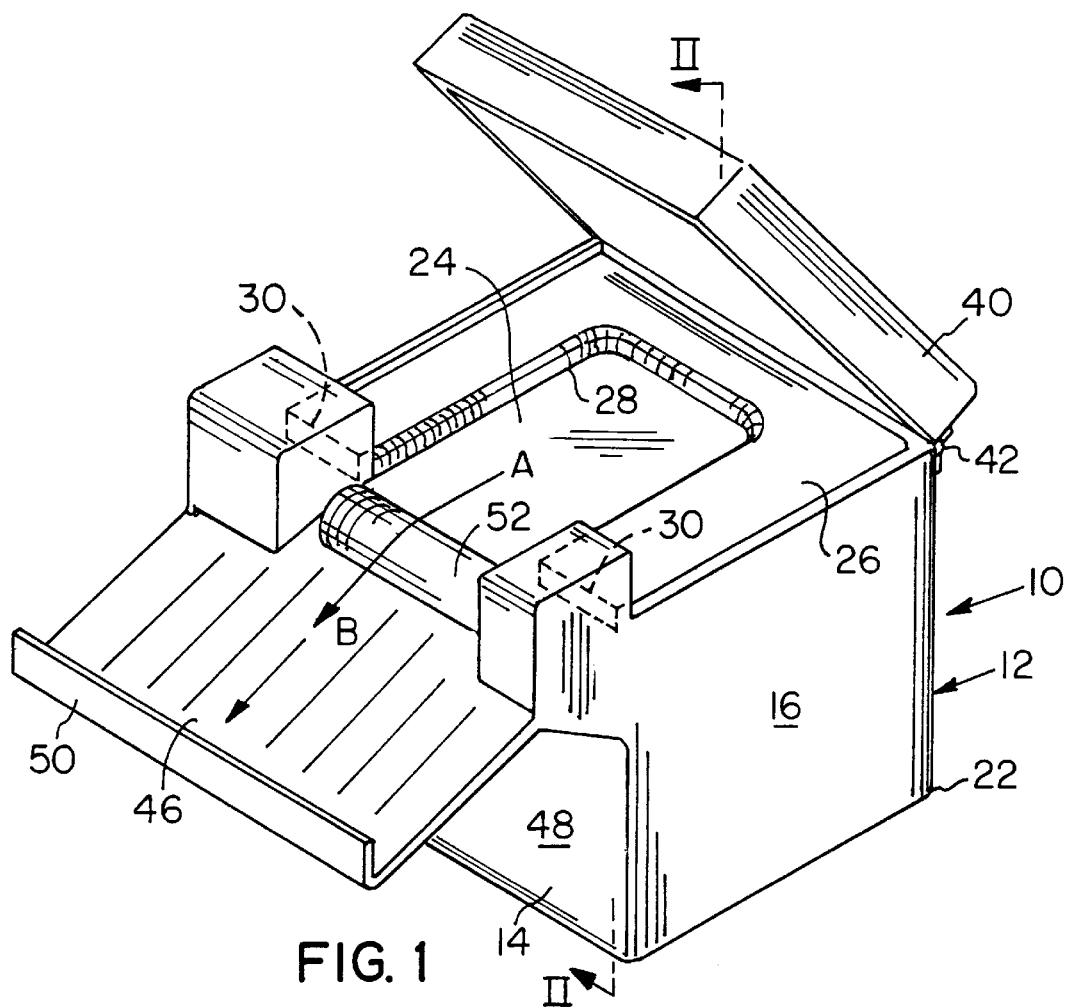
FIG. 1 is a top perspective view of a dispenser made in accordance with the present invention.
Figure 2:
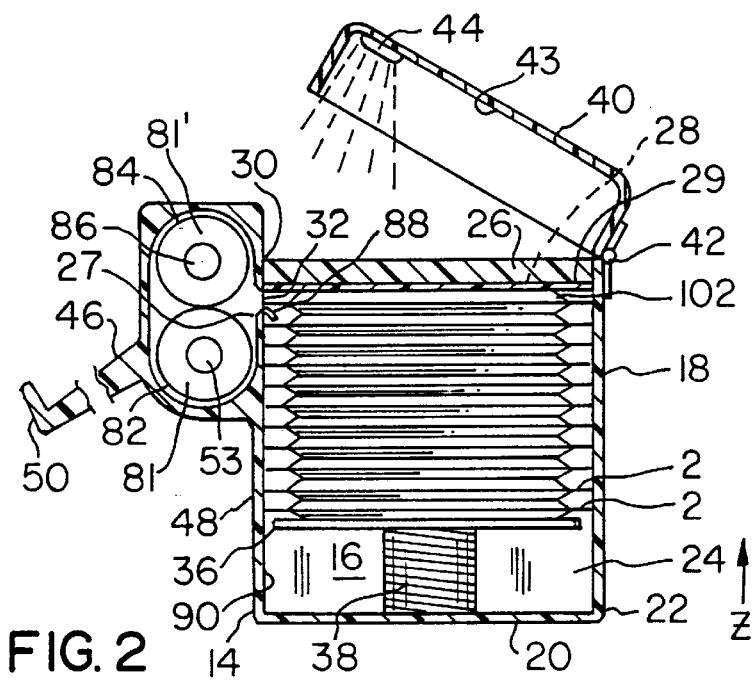
FIG. 2 is a side elevational sectional view taken along line II—II of the dispenser shown in FIG. 1.
Figure 3:
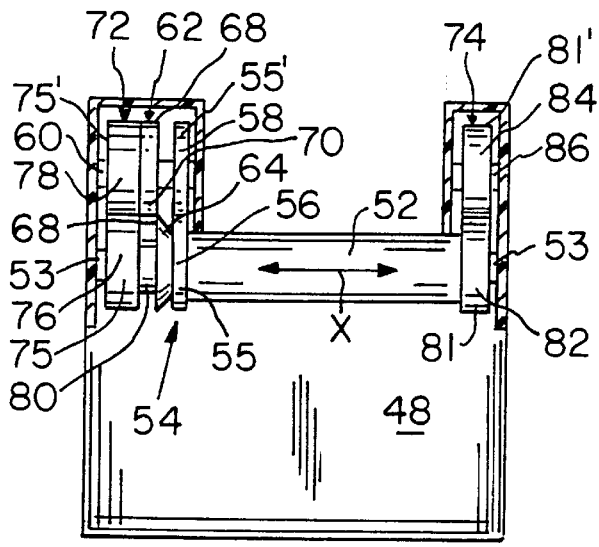
FIG. 3 is a front elevational view, partially in section, of the dispenser shown in FIG. 1.

FIGS. 1–3 show a dispenser 10 made in accordance with the present invention. The dispenser 10 is adapted to dispense one wrapped package 2 at a time and simultaneously cut open the package 2 to allow the user to easily remove the contents of the package 2.

Figure 4:
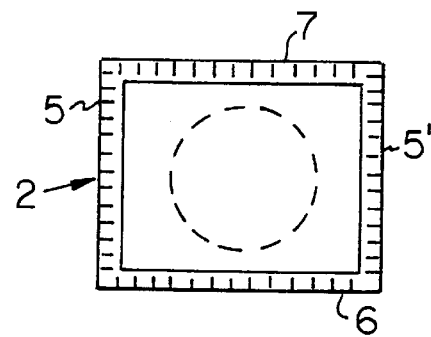
FIG. 4 is a top plan view of a package suitable for use with the dispenser shown in FIG. 1.
Figure 5:
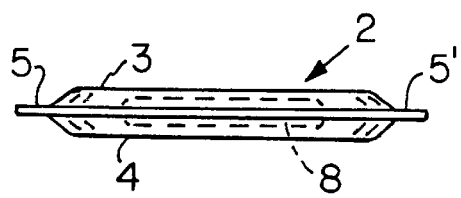
FIG. 5 is a side elevational view of the package shown in FIG. 4.

By wrapped package it is meant any article wrapped in a packaging material such as plastic, foil, cellophane and the like. FIGS. 4 and 5 show an exemplary wrapped package 2, a wrapped condom package, having an upper wrapper 3 and a lower wrapper 4. The package 2 has two sealed side edges 5 and 5', a sealed front edge 6 and a sealed rear edge 7 which seal together the upper wrapper 3 and lower wrapper 4 by crimping or with adhesives or by any other manner known in the art. The package 2 contains an article 8 shown in phantom in FIG. 5. The article 8 is loosely disposed within the package 2 such that when one of the sealed side edges 5 or 5', the sealed front edge 6 or the sealed rear edge 7 is opened, the article 8 is readily removed from the package 2.

Referring to FIGS. 1–3, the dispenser 10 includes a housing 12 with a front wall 14, two side walls 16 connected to the front wall 14 and a back wall 18 connected to the two side walls 16. A base 20 is connected to the front wall 14, the two side walls 16 and the back wall 18 at a first end 22 of the housing 12 to define a chamber 24. A lid 26 is removably secured to the housing 12 at a second end 27 of the housing 12 longitudinally spaced from the first end 22 in the Z direction. The lid 26 includes a U-shaped rim 28 which defines an upper opening shown at A into the chamber 24. The U-shaped rim 28 terminates in a pair of edges 30 (shown in phantom in FIG. 1) at the front wall 14 thereby defining a front opening 32 between the lid 26 and the front wall 14 at the second end 27. The lid 26 is supported by a support 29 which is fixed to inner surfaces of the housing 12 walls. The upper opening A is sized to be smaller than the upper wrapper 3 of the package 2.

A plate 36 is positioned within the chamber 24 and is adapted to slide against inner surfaces of the housing 12 walls. A biasing member or spring 38 is disposed between the base 20 and the plate 36.

The housing 12 includes a cover 40 which encloses the lid 26 and the upper opening A. The cover 40 is secured to the back wall 18 by a hinge 42. The hinge 42 may be placed anywhere along the cover 40 and connected to the back wall 18 or to the lid 26. An underside 43 of the cover 40 includes a light source 44 which illuminates when the cover 40 is opened. The light source 44 includes a light bulb (not shown) which is in turn connected to a switch (not shown) and a power source (not shown) in a manner known in the art.

A chute 46 is mounted on an outside surface 48 of the front wall 14 adjacent the front opening 32. The chute 46 terminates in a lip 50.

As shown in FIGS. 1 and 3, a drive roller 52, preferably made of rubber, is disposed between the edges 30 of the lid 26 and the chute 46 and is fixed onto a drive axle 53. The roller 52 extends along a longitudinal axis X adjacent the front opening 32.

Figure 7A:
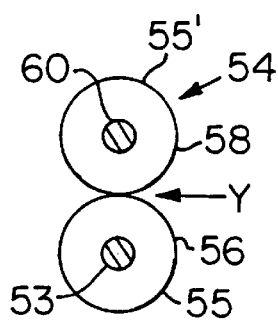
FIG. 7a is a side view of a portion of the dispenser shown in FIG. 1.

An aligning member 54 is disposed on one end of the roller 52. As shown in FIG. 7a, the aligning member 54 includes a pair of longitudinally spaced wheels 55 and 55' having aligning member surfaces 56 and 58, a portion of one of the aligning member surfaces 56 and 58 converging towards the other of the aligning member surfaces 56 and 58 in a second longitudinal direction Y. The aligning wheels 55 and 55' are preferably formed of rubber. The aligning wheel 55 is fixed to the drive axle 53. The aligning wheel 55' is fixed to a cutting axle 60 which is secured to the housing 12 parallel to the drive axle 53.

Figure 7B:
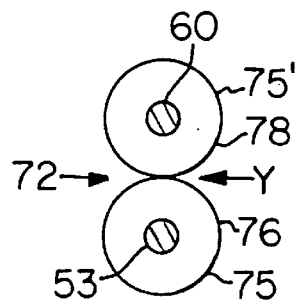
FIG. 7b is a side view of a portion of the dispenser shown in FIG. 1.

A cutting member 62 is disposed on an opposite side of the aligning member 54 from the roller 52. The cutting member 62 includes a pair of cutting disks 64 and 68, preferably formed of metal. The cutting disk 64 is frusto-conically shaped and mounted on the drive axle 53 on a side of the aligning wheel 56 opposite from the roller 52 and the cutting disk 68, which is circular shaped, is mounted on the cutting axle 60. The cutting disk 64 includes a cutting edge 66 and the cutting disk 68 includes a cutting surface 70 cooperating with the cutting edge 66 as shown in FIG. 7b.

Figure 7C:
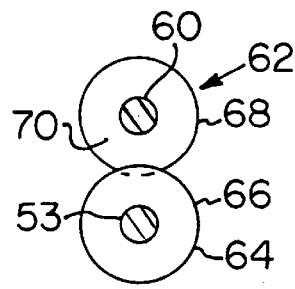
FIG. 7c is a side view of a portion of the dispenser shown in FIG. 1.

A pair of guiding members 72 and 74 are secured to the housing 12. The guiding member 72 is disposed on a side of the cutting member 62 opposite from the aligning member 54 and the guiding member 74 is disposed on a side of the roller 52 opposite from the aligning member 54. The guiding member 72 includes a pair of longitudinally spaced guiding wheels 75 and 75' having guiding member surfaces 76 and 78, a portion of one of the guiding member surfaces 76 and 78 converging towards the other of the guiding member surfaces 76 and 78 in the second longitudinal direction Y as shown in FIG. 7c. Preferably, the guiding wheels 75 and 75' are formed of rubber. The guiding wheel 75 is fixed to the drive axle 53. A spacer 80 is disposed on the drive axle 53 between the guiding wheel 75 and the cutting disk 64. The guiding wheel 75' is fixed to the cutting axle 60 adjacent the cutting disk 68.

The guiding member 74 likewise includes a pair of longitudinally spaced guiding wheels 81 and 81' having guiding member surfaces 82 and 84, a portion of one of the guiding member surfaces 82 and 84 converging towards the other of the guiding member surfaces 82 and 84 in the second longitudinal direction Y as shown in FIG. 2. Guiding wheels 81 and 81' are preferably formed of rubber. The guiding wheel 81 is fixed to the drive axle 53. The guiding wheel 81 is fixed to a guiding axle 86 secured to the housing 12 parallel to the drive axle 53.

A flexible tab 88 is mounted on an inside surface 90 of the front wall 14 below front opening 32. The tab 88 is sized to contact the upper wrapper 3 of package 2.

The operation of the dispenser 10 is set forth below. First, the lid 26 is removed from the housing 12. A plurality of the packages 2 are placed into the chamber 24 onto the plate 36. The lid 26 is then replaced onto the housing 12. The spring 38 urges the plate 36 and the packages 2 toward the lid 26, so that a top package 2 identified as 102 is exposed to the user through the upper opening A. The flexible tab 88 prevents the packages 2 other than the top package 102 from being withdrawn.

A user of the dispenser 10 containing the packages 2 places a thumb or other finger through the opening A onto the upper wrapper 3 of the top package 102. The top package 102 is withdrawn through the front opening 32 and over the drive roller 52 in the direction of the arrow B. The drive roller 52 rotates in response to the movement and pressure of the user's thumb or finger on the drive roller 52. Rotation of the drive roller 52 causes the drive axle 53 as well as the guiding wheels 75 and 81, the cutting disk 64 and the aligning wheel 55 to rotate.

As the package 102 is withdrawn from the front opening 32 and down the chute 46, the sealed side edge 5 of the top package 102 becomes drawn between the guiding wheels 75 and 75' and the sealed side edge 5' of the package 102 is drawn between the guiding wheels 81 and 81'. The movement of the edges 5 and 5' of the package 102 between the respective pairs of the guiding wheels 75 and 75' and the guiding wheels 81 and 81' causes the guiding wheels 75' and 81' to rotate, thereby rotating the cutting axle 60 and the guiding axle 86.

Figure 6:
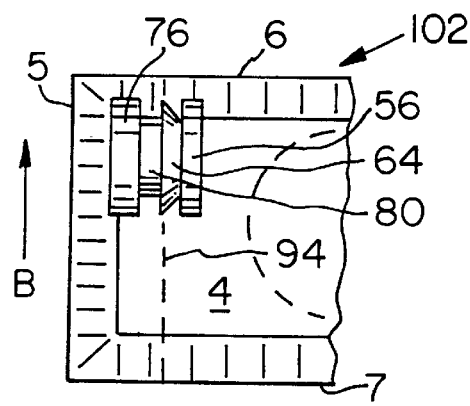
FIG. 6 is a bottom plan view of the package shown in FIG. 4 with a portion of the dispenser shown in FIG. 1.

Due to the rotation of the drive axle 53 and the cutting axle 60, the cutting disks 64 and 68 and the aligning wheels 55 and 55' rotate. As the sealed side edge 5 passes between the guiding wheels 75 and 75', the sealed side edge 5 is cut away from the package by the interaction between the cutting edge 66 and the cutting surface 70. The package 102 having the sealed side edge 5 cut away passes down the chute 46. The interaction between cutting disks 64 and 68 causes a cut to be made along cutting line 94 shown in dashed line in FIG. 6. As the package 102 advances in a direction of arrow B, the sealed side edge 5 is cut off from the package 102. The article 8 of the package 102 is then readily accessible. This process can be conveniently performed with one hand of the user.

The aligning wheels 55 and 55' contact the upper wrapper 3 and the lower wrapper 4 to position and push the article 8 within the package 102 away from the cutting disks 64 and 68 and between aligning member 54 and guiding member 74. Thus, the article 8 is protected by the action of the aligning wheels 55 and 55' from potential damage by the cutting disks 64 and 68.

The dispenser has been described with respect to packages such as condoms, but it can be made in a variety of sizes and shapes to accommodate various other individually wrapped packages. The exterior of the housing 12 may include an adhesive surface or clamp for mounting to a fixed object and it also may be decorative or disguised as another article for use in the home and the like.

Thus, the present invention includes a dispenser for individually wrapped articles which enhances the ease with which a sealed article is delivered to the user, thereby facilitating and/or encouraging the use of the article.

Although the present invention has been described in detail in connection with the discussed embodiment, various modifications may be made by one of ordinary skill in the art without departing from the spirit and scope of the present invention. Therefore, the scope of the present invention should be determined by the attached claims.

I claim:

1. A dispenser for wrapped packages each containing an article and having an edge, said dispenser comprising:

a housing defining a package receiving chamber, said housing including (i) a wall with an outer surface and an inner surface, (ii) a first end longitudinally spaced from a second end and (iii) a first opening defined at said second end for removal of the packages;

a biasing member secured to said housing and positioned within said package receiving chamber, said biasing member adapted to urge the packages in a first longitudinal direction toward said second end;

an aligning member secured to said housing and positioned adjacent said first opening, said aligning member comprising a pair of axially spaced aligning wheels rotatable mounted to said housing, wherein each said aligning wheel includes aligning surfaces, said aligning surfaces converging towards each other; and a cutting member having a cutting edge secured to said housing, whereby said biasing member is adapted to urge the packages toward said first opening so that a package can be pulled through said first opening, said aligning member positioning the article contained within the wrapped package away from said cutting member so that the wrapped package can be cut open by said cutting member edge for removal of the article from the cut-open wrapped package without said cutting edge contacting the article.

2. A dispenser as claimed in claim 1 further comprising a first guiding member secured to said housing and positioned adjacent said first opening, said first guiding member adapted to position the edge of the package adjacent said cutting member edge.

3. A dispenser as claimed in claim 2 wherein said first guiding member comprises a pair of longitudinally spaced guiding surfaces wherein at least a portion of one of said first guiding member surfaces converges towards the other of said first guiding surfaces in a second longitudinal direction.

4. A dispenser as claimed in claim 3 wherein said first guiding member comprises a pair of longitudinally spaced guiding wheels rotatably mounted to said housing wherein each of said guiding wheels includes one of said guiding surfaces.

5. A dispenser as claimed in claim 1 wherein said cutting member comprises a pair of axially spaced cutting disks rotatably mounted to said housing.

6. A dispenser as claimed in claim 5 wherein said cutting member is disposed adjacent said aligning member.

7. A dispenser as claimed in claim 1 wherein said biasing member is a spring.

8. A dispenser as claimed in claim 1 further comprising a roller extending along a longitudinal axis and rotatably mounted to said housing and adjacent said aligning member, said roller adapted to rotate about the longitudinal axis when the package is pulled through said first opening and contacts said roller.

9. A dispenser as claimed in claim 8 wherein said roller includes two opposing ends, said dispenser further comprising a pair of guiding members, each guiding member secured to said housing and having a set of converging surfaces positioned near the opposite ends of said roller, each set of converging surfaces including a pair of longitudinally spaced guiding surfaces wherein at least a portion of each said longitudinally spaced guiding surfaces converges towards the other of said pair of longitudinally spaced guiding surfaces in a second longitudinal direction.

10. A dispenser as claimed in claim 9 wherein each of said guiding members comprise a pair of guiding wheels, each of said guiding wheels including one of said guiding surfaces.

11. The dispenser as claimed in claim 8 further comprising a chute mounted on said outer surface of said wall adjacent said roller and adapted to receive the packages.

12. A dispenser as claimed in claim 1 further comprising a lid secured to said housing and defining with said housing said first opening.

13. A dispenser as claimed in claim 12 wherein said lid includes a U-shaped inner rim having an edge adjacent said wall and defining a second opening.

14. A dispenser as claimed in claim 13 further comprising a tab extending from said wall inner surface into said chamber and adapted to contact one of the packages at a distance from said lid.

15. A dispenser as claimed in claim 12 further comprising a cover pivotally secured to said lid.

16. A dispenser as claimed in claim 15 further comprising a light source mounted to said cover.

17. A dispenser for wrapped packages each containing an article and having two opposing edges, said dispenser comprising:

a housing defining a package receiving chamber, said housing including (i) a wall with an outer surface and an inner surface, (ii) a first end longitudinally spaced from a second end, (iii) a lid secured to said housing at said second end and defining an opening for removal of the packages and (iv) a cover pivotally secured to said lid;

a biasing member secured to said housing and positioned within said package receiving chamber, said biasing member adapted to urge the packages in a first longitudinal direction toward said second end;

an aligning member secured to said housing and positioned adjacent said first openings, said aligning member comprising a pair of axially spaced aligning wheels rotatable mounted to said housing, wherein each said aligning wheel includes an aligning surfaces, said aligning surfaces converging towards each other;

a roller having two opposing ends, said roller extending along a longitudinal axis and being rotatably mounted to said housing and adjacent said aligning member;

a first guiding member adapted to position one of the package edges adjacent said cutting member edge and secured to said housing adjacent said roller;

a second guiding member adapted to position the other package edge and secured to said housing on a side of said aligned member opposite said roller;

a cutting member having a cutting edge secured to said housing, said cutting member disposed between said aligning member and said first guiding member;

a chute mounted on said wall outer surface adjacent said roller and adapted to receive the packages; and a tab extending from said wall inner surface into said chamber and adapted to contact one of the packages at a distance from said lid.

\* \* \* \* \*

UNITED STATES PATENT AND TRADEMARK OFFICE
CERTIFICATE OF CORRECTION

PATENT NO. : 5,806,278
DATED : September 15, 1998
INVENTOR(S) : Guy R. Shelledy

It is certified that error appears in the above-identified patent and that said Letters Patent is hereby corrected as shown below:

Column 1 Line 53 after "disclosed in" delete period --.--.

Column 2 Line 2 "alleviate" should read --alleviates--.

Column 2 Line 9 "describe" should read --describes--.

Column 3 Line 5 "are" should read --is--.

Column 4 Line 59 "are" should read --is--.

Column 5 Lines 15-16 "The guiding wheel 81" should read --The guiding wheel 81'--.

Column 5 Line 23 "are placed" should read --is placed--.

Claim 1 Column 6 Line 37 "rotatable mounted" should read --rotatably mounted--.

Claim 10 Column 7 Line 22 "comprise" should read --comprises--.

Signed and Sealed this

Sixteenth Day of February, 1999

Attest:

Attesting Officer

*Acting Commissioner of Patents and Trademarks*